(12) United States Patent
Gomes et al.

(10) Patent No.: US 7,067,123 B2
(45) Date of Patent: Jun. 27, 2006

(54) GLUE FOR CARTILAGE REPAIR

(75) Inventors: Katherine A. Gomes, Somerville, NJ (US); Moon Hae Sunwoo, Old Tappan, NJ (US); Arthur A. Gertzman, Stony Point, NY (US)

(73) Assignee: Musculoskeletal Transplant Foundation, Edison, NJ (US)

( * ) Notice: Subject to any disclaimer, the term of this patent is extended or adjusted under 35 U.S.C. 154(b) by 463 days.

(21) Appl. No.: 10/424,765

(22) Filed: Apr. 29, 2003

(65) Prior Publication Data
US 2004/0219182 A1 Nov. 4, 2004

(51) Int. Cl.
*A61K 35/32* (2006.01)

(52) U.S. Cl. .................. 424/93.7; 424/548

(58) Field of Classification Search ........... 424/93.7
See application file for complete search history.

(56) References Cited

U.S. PATENT DOCUMENTS

| | | | |
|---|---|---|---|
| 4,172,128 A | 10/1979 | Thiele et al. | |
| 4,950,296 A | 8/1990 | McIntyre | |
| 5,073,373 A | 12/1991 | O'Leary et al. | |
| 5,290,558 A | 3/1994 | O'Leary et al. | |
| 5,314,476 A | 5/1994 | Prewett et al. | |
| 5,356,629 A | 10/1994 | Sander et al. | |
| 5,507,813 A | 4/1996 | Dowd et al. | |
| 6,030,635 A | 2/2000 | Gertzman et al. | |
| 6,039,762 A | 3/2000 | McKay | |
| 6,096,081 A | 8/2000 | Grivas et al. | |
| 6,110,209 A | 8/2000 | Stone | |
| 6,294,187 B1 | 9/2001 | Boyce et al. | |
| 6,379,367 B1 | 4/2002 | Vibe-Hansen et al. | |
| 6,379,385 B1 | 4/2002 | Kalas et al. | |
| 6,383,221 B1 | 5/2002 | Scarborough et al. | |
| 6,398,811 B1 | 6/2002 | McKay | |
| 6,437,018 B1 | 8/2002 | Gertzman et al. | |
| 6,689,747 B1 | 2/2004 | Filvaroff et al. | |
| 6,761,887 B1 | 7/2004 | Kavalkovich et al. | |
| 6,838,440 B1* | 1/2005 | Stiles ..................... | 514/21 |
| 2004/0192605 A1 | 9/2004 | Zhang et al. | |
| 2004/0230303 A1* | 11/2004 | Gomes et al. ......... | 623/16.11 |
| 2005/0159822 A1 | 7/2005 | Griffey et al. | |

FOREIGN PATENT DOCUMENTS

| | | |
|---|---|---|
| WO | WO 03/007805 A2 | 1/2003 |
| WO | WO 03/007879 A2 | 1/2003 |
| WO | WO 2003/007805 A3 | 1/2003 |

OTHER PUBLICATIONS

Feczkó et al., "Experimental Results of Donor Site Filling for Autologous Osteochondral Mosaicplasty", Arthroscopy: The Journal of Arthroscopic and Related Surgery, vol. 19, No. 7 (Sep., 2003), pp. 755-761.

(Continued)

*Primary Examiner*—Jean C. Witz
(74) *Attorney, Agent, or Firm*—John S. Hale; Gipple & Hale

(57) ABSTRACT

The invention is directed toward a sterile cartilage defect implant material comprising milled lyophilized allograft cartilage pieces ranging from 0.01 mm to 1.0 mm in size in a bioabsorbable carrier taken from a group consisting of sodium hyaluronate, hyaluronic acid and its derivatives, gelatin, collagen, chitosan, alginate, buffered PBS, Dextran or polymers with allogenic chondrocytes or bone marrow cells in an amount exceeding the natural occurrence of same in hyaline cartilage and adding a cell growth additive.

39 Claims, 1 Drawing Sheet

OTHER PUBLICATIONS

Nettles et al., "In Situ Crosslinkable Hyaluronan For Articular Cartilage Repair", 50th Annual Meeting of the Orthopaedic Resarch Society, Paper No. 2020.

Nettles et al., "Photocrosslinkable Hyaluronan As a Scaffold for Articular Cartilage Repair", Annals of Biomedical Engineering, vol. 32, No. 3, Mar. 2004, pp. 391-397.

Verbruggen et al., "Repair Function in Organ Cultured Human Cartilage. Replacement fo Enzymatically Removed Proteoglycans During Longterm Organ Culture", The Journal of Rheumatology, 12:4, (1985), pp. 665-674.

Chen et al., "Repair of Articular Cartilage Defects: Part 1. Basic Science of Cartilage Healing", The American Journal of Orthopaedics (Jan. 1999) pp. 31-33.

Jackson et al., "Cartilage Substitute: Overview of Basic Science & Treatment Options", Journal of American Academy of Orthopaedic Surgeons, vol. 9 (Jan./Feb. 2001) pp. 37-52.

Peretti et al., "Cell-Based Bonding of Articular Cartilage: An Extended Study", Wiley Publications, Inc., 2003 pp. 517-524.

* cited by examiner

GLUE FOR CARTILAGE REPAIR

RELATED APPLICATIONS

There is no related application.

1. Field of Invention

The present invention is generally directed toward an implant and is more specifically directed toward a paste or gel implant material for a cartilage defect.

2. Background of the Invention

Articular cartilage injury and degeneration present medical problems to the general population which are addressed by orthopedic surgeons. Every year in the United States, over 500,000 arthroplastic or joint repair procedures are performed. These include approximately 125,000 total hip and 150,000 total knee arthroplastics and over 41,000 open arthroscopic procedures to repair cartilaginous defects of the knee.

In the knee joint, the articular cartilage tissue forms a lining which faces the joint cavity on one side and is linked to the subchondral bone plate by a narrow layer of calcified cartilage tissue on the other. Articular cartilage (hyaline cartilage) consists primarily of extracellular matrix with a sparse population of chondrocytes distributed throughout the tissue. Articular cartilage is composed of chondrocytes, type II collagen fibril network, proteoglycans and water. Active chondrocytes are unique in that they have a relatively low turnover rate and are sparsely distributed within the surrounding matrix. The collagens give the tissue its form and tensile strength and the interaction of proteoglycans with water give the tissue its stiffness to compression, resilience and durability. The hyaline cartilage provides a low friction bearing surface over the bony parts of the joint. If the lining becomes worn or damaged resulting in lesions, joint movement may be painful or severely restricted. Whereas damaged bone typically can regenerate successfully, hyaline cartilage regeneration is quite limited because of it's limited regenerative and reparative abilities.

Articular cartilage lesions generally do not heal, or heal only partially under certain biological conditions due to the lack of nerves, blood vessels and a lymphatic system. The limited reparative capabilities of hyaline cartilage usually results in the generation of repair tissue that lacks the structure and biomechanical properties of normal cartilage. Generally, the healing of the defect results in a fibrocartilaginous repair tissue that lacks the structure and biomedical properties of hyaline cartilage and degrades over the course of time. Articular cartilage lesions are frequently associated with disability and with symptoms such as joint pain, locking phenomena and reduced or disturbed function. These lesions are difficult to treat because of the distinctive structure and function of hyaline cartilage. Such lesions are believed to progress to severe forms of osteoarthritis. Osteoarthritis is the leading cause of disability and impairment in middle-aged and older individuals, entailing significant economic, social and psychological costs. Each year, osteoarthritis accounts for as many as 39 million physician visits and more than 500,000 hospitalizations. By the year 2020, arthritis is expected to affect almost 60 million persons in the United States and to limit the activity of 11.6 million persons.

There are many current therapeutic methods being used. None of these therapies has resulted in the successful regeneration of hyaline-like tissue that withstands normal joint loading and activity over prolonged periods. Currently, the techniques most widely utilized clinically for cartilage defects and degeneration are not articular cartilage substitution procedures, but rather lavage, arthroscopic debridement, and repair stimulation. The direct transplantation of cells or tissue into a defect and the replacement of the defect with biologic or synthetic substitutions presently accounts for only a small percentage of surgical interventions. The optimum surgical goal is to replace the defects with cartilage-like substitutes so as to provide pain relief, reduce effusions and inflammation, restore function, reduce disability and postpone or alleviate the need for prosthetic replacement.

Lavage and arthroscopic debridement involve irrigation of the joint with solutions of sodium chloride, Ringer or Ringer and lactate. The temporary pain relief is believed to result from removing degenerative cartilage debris, proteolytic enzymes and inflammatory mediators. These techniques provide temporary pain relief, but have little or no potential for further healing.

Repair stimulation is conducted by means of drilling, abrasion arthroplasty or microfracture. Penetration into the subchondral bone induces bleeding and fibrin clot formation which promotes initial repair, however, the tissue formed is fibrous in nature and not durable. Pain relief is temporary as the tissue exhibits degeneration, loss of resilience, stiffness and wear characteristics over time.

The periosteum and perichondrium have been shown to contain mesenchymal progenitor cells capable of differentiation and proliferation. They have been used as grafts in both animal and human models to repair articular defects. Few patients over 40 years of age have obtained good clinical results, which most likely reflects the decreasing population of osteochondral progenitor cells with increasing age. There have also been problems with adhesion and stability of the grafts, which result in their displacement or loss from the repair site.

Transplantation of cells grown in culture provides another method of introducing a new cell population into chondral and osteochondral defects. Carticel® is a commercial process to culture a patient's own cartilage cells for use in the repair of cartilage defects in the femoral condyle marketed by Genzyme Biosurgery in the United States and Europe. The procedure uses arthroscopy to take a biopsy from a healthy, less loaded area of articular cartilage. Enzymatic digestion of the harvested tissue releases the cells that are sent to a laboratory where they are grown for a period ranging from 2–5 weeks. Once cultivated, the cells are injected during a more open and extensive knee procedure into areas of defective cartilage where it is hoped that they will facilitate the repair of damaged tissue. An autologous periosteal flap with cambium layer is used to seal the transplanted cells in place and act as a mechanical barrier. Fibrin glue is used to seal the edges of the flap. This technique preserves the subchondral bone plate and has reported a high success rate. Proponents of this procedure report that it produces satisfactory results, including the ability to return to demanding physical activities, in more than 90% of patients and that biopsy specimens of the tissue in the graft sites show hyaline-like cartilage repair. More work is needed to assess the function and durability of the new tissue and determine whether it improves joint function and delays or prevents joint degeneration. As with the perichondrial graft, patient/donor age may compromise the success of this procedure as chondrocyte population decreases with increasing age. Disadvantages to this procedure include the need for two separate surgical procedures, potential damage to surrounding cartilage when the periosteal patch is sutured in place, the requirement of demanding microsurgical techniques, and the expensive cost of the procedure which is currently not covered by insurance.

Osteochondral transplantation or mosaicplasty involves excising all injured or unstable tissue from the articular defect and creating cylindrical holes in the base of the defect and underlying bone. These holes are filled with autologous cylindrical plugs of healthy cartilage and bone in a mosaic fashion. The osteochondral plugs are harvested from a lower weight-bearing area of lesser importance in the same joint. This technique, shown in Prior Art FIG. 2, can be performed as arthroscopic or open procedures. Reports of results of osteochondral plug autografts in a small number of patients indicate that they decrease pain and improve joint function, however, long-term results have not been reported. Factors that can compromise the results include donor site morbidity, effects of joint incongruity on the opposing surface of the donor site, damage to the chondrocytes at the articular margins of the donor and recipient sites during preparation and implantation, and collapse or settling of the graft over time. The limited availability of sites for harvest of osteochondral autografts restricts the use of this approach to treatment of relatively small articular defects and the healing of the chondral portion of the autograft to the adjacent articular cartilage remains a concern.

Transplantation of large allografts of bone and overlying articular cartilage is another treatment option that involves a greater area than is suitable for autologous cylindrical plugs, as well as for a non-contained defect. The advantages of osteochondral allografts are the potential to restore the anatomic contour of the joint, lack of morbidity related to graft harvesting, greater availability than autografts and the ability to prepare allografts in any size to reconstruct large defects. Clinical experience with fresh and frozen osteochondral allografts shows that these grafts can decrease joint pain, and that the osseous portion of an allograft can heal to the host bone and the chondral portion can function as an articular surface. Drawbacks associated with this methodology in the clinical situation include the scarcity of fresh donor material and problems connected with the handling and storage of frozen tissue. Fresh allografts carry the risk of immune response or disease transmission. Musculoskeletal Transplant Foundation (MTF) has preserved fresh allografts in a media that maintains a cell viability of 50% for 35 days for use as implants. Frozen allografts lack cell viability and have shown a decreased amount of proteoglycan content which contribute to deterioration of the tissue.

A number of patents in the prior art show the use of bone putty, pastes or gels to fill bone defects. U.S. Pat. No. 5,290,558 issued Mar. 1, 1994 discloses a flowable demineralized bone powder composition using an osteogenic bone powder with large particle size ranging from about 0.1 to about 1.2 cm. mixed with a low molecular weight polyhydroxy compound possessing from 2 to about 18 carbons including a number of classes of different compounds such as monosaccharides, disaccharides, water dispersible oligosaccharides and polysaccharides.

A bone gel is disclosed in the U.S. Pat. No. 5,073,373 issued Dec. 17, 1991. Bone lamellae in the shape of threads or filaments retaining low molecular weight glycerol carrier are disclosed in U.S. Pat. Nos. 5,314,476 issued May 24, 1994 and 5,507,813 issued Apr. 16, 1996 and the tissue forms described in these patents are known commercially as the GRAFTON® Putty and Flex, respectively.

U.S. Pat. No. 5,356,629 issued Oct. 18, 1994 discloses making a rigid gel in the nature of a bone cement to fill defects in bone by mixing biocompatible particles, preferably polymethylmethacrylate coated with polyhydroxyethylmethacrylate in a matrix selected from a group which lists hyaluronic acid to obtain a molded semi-solid mass which can be suitably worked for implantation into bone. The hyaluronic acid can also be utilized in monomeric form or in polymeric form preferably having a molecular weight not greater than about one million Daltons. It is noted that the nonbioabsorbable material which can be used to form the biocompatible particles can be derived from xenograft bone, homologous bone, autogenous bone as well as other materials. The bioactive substance can also be an osteogenic agent such as demineralized bone powder, morselized cancellous bone, aspirated bone marrow and other autogenous bone sources. The average size of the particles employed is preferably about 0.1 to about 3.0 mm, more preferably about 0.2 to about 1.5 mm, and most preferably about 0.3 to about 1.0 mm. It is inferentially mentioned but not taught that particles having average sizes of about 7,000 to 8,000 microns, or even as small as about 100 to 700 microns can be used.

U.S. Pat. No. 4,172,128 issued Oct. 23, 1979 discloses a demineralized bone material mixed with a carrier to reconstruct tooth or bone material by adding a mucopolysaccharide to a mineralized bone colloidal material. The composition is formed from a demineralized coarsely ground bone material, which may be derived from human bones and teeth, dissolved in a solvent forming a colloidal solution to which is added a physiologically inert polyhydroxy compound such as mucopolysaccharide or polyuronic acid in an amount which causes orientation when hydrogen ions or polyvalent metal ions are added to form a gel. The gel will be flowable at elevated temperatures above 35° C. and will solidify when brought down to body temperature. Example 25 of the patent notes that mucopolysaccharides produce pronounced ionotropic effects and that hyaluronic acid is particularly responsible for spatial cross-linking.

U.S. Pat. No. 6,030,635 issued Feb. 29, 2000 and U.S. Pat. No. 6,437,018 issued Aug. 20, 2002 are directed toward a malleable bone putty and a flowable gel composition for application to a bone defect site to promote new bone growth at the site which utilize a new bone growth inducing compound of demineralized lyophilized allograft bone powder. The bone powder has a particle size ranging from about 100 to about 850 microns and is mixed in a high molecular weight hydrogel carrier which contains a sodium phosphate saline buffer.

The use of implants for cartilage defects is much more limited. Aside from the fresh allograft implants and autologous implants, U.S. Pat. No. 6,110,209 issued Nov. 5, 1998 shows the use an autologous articular cartilage cancerous bone paste to fill arthritic defects. The surgical technique is arthroscopic and includes debriding (shaving away loose or fragmented articular cartilage), followed by morselizing the base of the arthritic defect with an awl until bleeding occurs. An osteochondral graft is then harvested from the inner rim of the intercondylar notch using a trephine. The graft is then morselized in a bone graft crusher, mixing the articular cartilage with the cancellous bone. The paste is then pushed into the defect and secured by the adhesive properties of the bleeding bone. The paste can also be mixed with a cartilage stimulating factor, a plurality of cells, or a biological glue. All patients are kept non-weight bearing for four weeks and used a continuous passive motion machine for six hours each night. Histologic appearance of the biopsies have mainly shown a mixture of fibrocartilage with hyaline cartilage. Concerns associated with this method are harvest site morbidity and availability, similar to the mosaicplasty method.

SUMMARY OF THE INVENTION

A cartilage implant material in paste or gel form for repairing articular cartilage defects is composed of milled allograft cartilage pieces in a bioabsorbable carrier. Autologous chondrocyte in an amount exceeding the number naturally occurring in hyaline cartilage for a mature adult between 20 and 55 years of age may also be applied to the matrix. Additives may be applied to the mixture in order to increase chondrocyte migration and proliferation. The implant material can support the addition of a variety of chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic or autologous bone marrow cells, stem cells, demineralized bone matrix, insulin, insulin-like growth factor-1, transforming growth factor-B, interleukin-1 receptor antagonist, hepatocyte growth factor, platelet-derived growth factor, Indian hedgehog and parathyroid hormone-related peptide or bioactive glue.

The implant material is placed in the lesion area and may be sealed with a periosteum cap.

It is an object of the invention to provide an allograft implant material for joints which provides pain relief, restores normal function and will postpone or alleviate the need for prosthetic replacement.

It is also an object of the invention to provide a cartilage repair implant material which is easily placed in a defect area by the surgeon using an arthroscopic, minimally invasive technique.

It is further an object of the invention to provide an allograft implant material procedure which is applicable for both partial and full thickness lesions.

It is yet another object of the invention to provide an allograft implant material which facilitates growth of hyaline cartilage.

It is an additional object of the invention to provide implant paste and gel material formulations that satisfy surgical requirements and are made from donated human available allograft tissue, some of which would otherwise be considered waste and thrown away.

These and other objects, advantages, and novel features of the present invention will become apparent when considered with the teachings contained in the detailed disclosure along with the accompanying drawings.

DESCRIPTION OF THE INVENTION

The terms "tissue" is used in the general sense herein to mean any transplantable or implantable tissue, the survivability of which is improved by the methods described herein upon implantation. In particular, the overall durability and longevity of the implant are improved, and host-immune system mediated responses, are substantially eliminated.

The terms "transplant" and "implant" are used interchangably to refer to tissue, material or cells (xenogeneic or allogeneic) which may be introduced into the body of a patient to replace or supplement the structure or function of the endogenous tissue.

The terms "autologous" and "autograft" refer to tissue or cells which originate with or are derived from the recipient, whereas the terms "allogeneic" and "allograft" refer to cells and tissue which originate with or are derived from a donor of the same species as the recipient. The terms "xenogeneic" and "xenograft" refer to cells or tissue which originates with or is derived from a species other than that of the recipient.

The term "gel" refers to a mixture of minced or milled pretreated allograft cartilage in a biocomposite carrier having a viscosity which is less than and is less rigid than a mixture of minced or milled pretreated allograft cartilage in a biocompatible carrier referred to by the terms "putty" or "paste" and contains less cartilage by weight than putty or paste.

Figure 1:
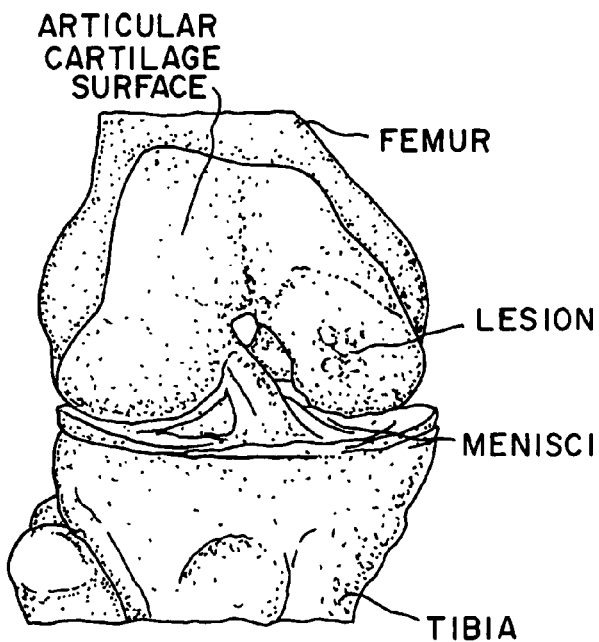
FIG. 1 shows the anatomy of a knee joint with a lesion.
Figure 2:
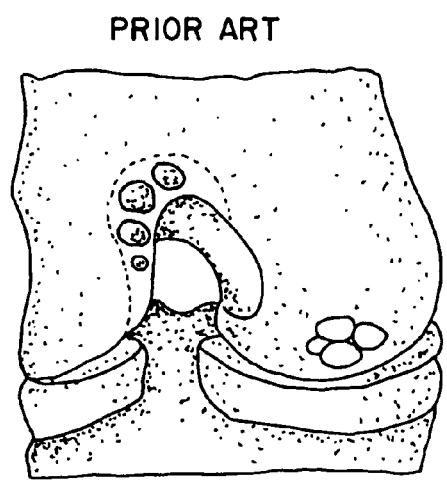
FIG. 2 shows a schematic mosaicplasty as known in the prior art.
Figure 3:
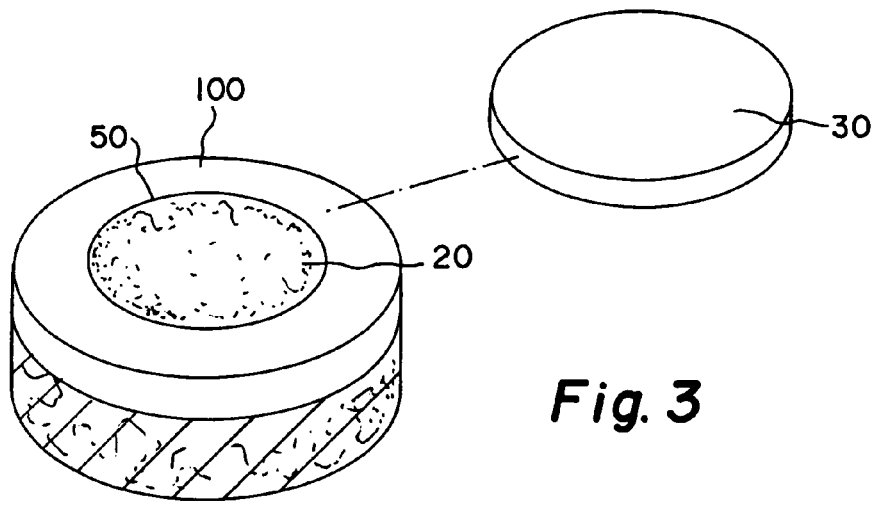
FIG. 3 shows a schematic perspective view of cartilage defect material placed in a defect site with an exploded periosteum cap.

The present invention is directed towards a cartilage repair material and method of treatment. The preferred embodiment and best mode of the invention is shown in FIG. 3. In the production of the invention, allograft hyaline cartilage is lyophilized reducing its water content and milled for ease in application.

After washes with sterile de-ionized (DI) water, the cartilage material was frozen at −20° to −100° C. preferably −70° C. and lyophilized to reduce the water content within the range of about 0.1% to about 8.0%. The cartilage is frozen with liquid nitrogen and ground into particles.

A lesion or defect is removed by cutting a bore 50 or trimming a lesion in the implant area 100 and filling the bore 50 or lesion area with a milled cartilage mixture 20 of paste or gel consisting together with a biological carrier such as hyaluronic acid and its derivatives, gelatin, collagen, chitosan, alginate, buffered PBS, Dextran, or polymers and one or more additives namely chondrogenic stimulating factors including, but not limited to growth factors (FGF-2, FGF-5, IGF-1, TGF-β, BMP-2, BMP-7, PDGF, VEGF), human allogenic or autologous chondrocytes, human allogenic cells, human allogenic or autologous bone marrow cells, human allogenic or autologous stem cells, demineralized bone matrix, insulin, insulin-like growth factor-1, interleukin-1 receptor antagonist, hepatocyte growth factor, platelet-derived growth factor, Indian hedgehog and parathyroid hormone-related peptide.

Suitable organic glue material can be used to keep the viscous cartilage mixture 20 fixed in place in the implant area or to affix a periosteal cap 30 in place over the surrounding hyaline cartilage area 100. Suitable organic glue material can be found commercially, such as for example; TISSEEL® or TISSUCOL.®) (fibrin based adhesive; Immuno AG, Austria), Adhesive Protein (Sigma Chemical, USA), and Dow Corning Medical Adhesive B (Dow Corning, USA).

EXAMPLE 1

A matrix of minced cartilage putty consisting of minced or milled allograft articular cartilage which has been lyophilized so that its water content ranges from 0.1% to 8.0% with a cartilage content ranging from 25% to 50% by weight is mixed with a carrier of sodium hyaluronate solution (HA) (molecular weight ranging from $7.0 \times 10^5$ to $1.2 \times 10^6$) or any other bioabsorbable carrier such as hyaluronic acid and its derivatives, gelatin, collagen, chitosan, alginate, buffered PBS, Dextran, or polymers, the carrier ranging from 75% to 50% by weight. The cartilage is milled to a size ranging from 0.01 mm to 1 mm. In gel form, the minced cartilage which has been lyophilized so that its water content ranges from 0.1% to 8.0% ranging from 15% to 30% by weight and the carrier ranges from 85% to 70% by weight. The particle size of the cartilage when milled is less than or equal to 1 mm dry in the previously stated range. The cartilage pieces can be processed to varying particle sizes and the HA or other carrier can have different viscosities depending on the desired consistency of the putty or paste. This cartilage matrix can be deposited into the cartilage defect arthroscopically and fit into the defect where it is held in place by it's own viscosity, mixed with fibrin glue or covered with a periosteal or perichondrial flap, then sealed with biological glue. As with the first two matrices, this matrix can support the previously mentioned chondrogenic factors.

EXAMPLE 2

A matrix of minced cartilage putty consisting of minced or milled allograft cartilage which has been lyophilized so that its water content ranges from 0.1% to 8.0% ranging from 25% to 50% by weight is mixed with a carrier of sodium hyaluronate solution (HA) ($7.0 \times 10^5$ to $1.2 \times 10^6$) or any other bioabsorbable carrier such as hyaluronic acid and its derivatives, gelatin, collagen, chitosan, alginate, buffered PBS, Dextran, or polymers ranging from 75% to 50% by weight. In a gel form, the minced cartilage which has been lyophilized so that its water content ranges from 0.01% to 8.0% ranging from 15% to 30% by weight and the carrier ranges from 85% to 70% by weight. The particle size of the cartilage is less than or equal to 1 mm dry ranging from 0.01 mm to 1 mm. The cartilage pieces can be processed to varying particle sizes and the HA or carrier can have different viscosities depending on the desired consistency of the putty or paste. Autologous or allogenic cells which have been grown outside the patient are inserted by syringe into the matrix before, during or after deposit of the cartilage matrix into the defect area. Such cells include allogenic or autologous bone marrow cells, stem cells and chondrocyte cells. The cellular density of the cells preferably ranges from about $1 \times 10^8$ to $5 \times 10^8$ or from about 100 million to about 500 million cells per cc of putty or gel mixture. This composite material can be injected into the cartilage defect arthroscopically and fit into the defect where it is held in place by it's own viscosity, or covered with a periosteal or perichondrial flap, then sealed with biological glue. As with the first matrix, this matrix can support the previously mentioned chondrogenic factors.

The operation of placing the cartilage composition in a cartilage defect, comprises (a) cutting a patient's tissue at a site of a cartilage defect to remove the diseased area of cartilage; (b) placing a mixture of milled allograft cartilage in a bioabsorbable carrier in the defect area; and (c) placing a periosteal cover over the mixture of the inserted milled allograft cartilage in a bioabsorbable carrier to contain the mixture in the defect area for a predetermined period of time to promote cartilage growth at the defect site. Alternate steps include the addition of growth factors, chondrocytes, bone marrow cells and stem cells.

The principles, preferred embodiments and modes of operation of the present invention have been described in the foregoing specification. However, the invention should not be construed as limited to the particular embodiments which have been described above. Instead, the embodiments described here should be regarded as illustrative rather than restrictive.

What we claim is:

1. A sterile allograft cartilage defect implant material for use in human beings comprising milled allograft cartilage pieces sized less than 1 mm and lyophilized so that their water content ranges from about 0.1% to about 8.0% in a bioabsorbable carrier.

2. A sterile allograft cartilage defect implant material as claimed in claim 1 wherein said milled cartilage ranges from about 25% to about 50% by weight and said carrier ranges from about 75% to about 50% by weight.

3. A sterile allograft cartilage defect implant material as claimed in claim 1 wherein said milled cartilage ranges from about 15% to about 30% by weight with the carrier ranging from about 85% to about 70% by weight.

4. A sterile allograft cartilage defect implant material as claimed in claim 1 wherein said carrier is sodium hyaluronate and its derivatives.

5. A sterile allograft cartilage defect implant material as claimed in claim 1 wherein said implant material includes a protein glue.

6. A sterile allograft cartilage defect implant material as claimed in claim 1 wherein said implant material includes the addition of autologous chondrocytes to achieve a concentration exceeding the concentration of chondrocytes naturally occurring in the patient.

7. A sterile allograft cartilage defect implant material as claimed in claim 1 wherein said milled cartilage is hyaline cartilage.

8. A sterile allograft cartilage defect implant material as claimed in claim 1 wherein said milled cartilage is fibrosus cartilage.

9. A sterile allograft cartilage defect implant material as claimed in claim 1 wherein said milled cartilage is hyaline and fibrosus cartilage.

10. A sterile allograft cartilage defect implant material claimed in claim 1 including an additive to said implant material consisting of one or more of a group consisting of growth factors, human allogenic cells, human allogenic bone marrow cells, human autologous bone marrow cells, human allogenic stem cells, human autologous stem cells, human demineralized bone matrix, and insulin.

11. A sterile cartilage repair material as claimed in claim 10 wherein said growth factors are one or more of a group consisting of FGF-2, FGF-5, IGF-1, TGF-$\beta$, BMP-2, BMP-7, PDGF, VEGF.

12. A sterile allograft cartilage defect implant material as claimed in claim 1 wherein said carrier comprises one or more bioabsorbable carriers taken from a group consisting of sodium hyaluronate, hyaluronic acid and its derivatives, gelatin, collagen, chitosan, alginate, buffered PBS, Dextran or polymers.

13. A sterile cartilage defect implant material comprising milled allograft articular cartilage pieces ranging from 0.01 mm to 1.0 mm in size in a bioabsorbable carrier taken from a group consisting of sodium hyaluronate, gelatin, collagen, chitosan, alginate, buffered PBS, Dextran or polymers and allogenic chondrocytes in an amount exceeding the natural occurrence of same in articular cartilage.

14. A sterile cartilage defect implant material as claimed in claim 13 wherein said allograft articular cartilage is hyaline cartilage.

15. A sterile allograft cartilage defect implant material as claimed in claim 13 wherein said milled cartilage is fibrous cartilage.

16. A sterile allograft cartilage defect implant material as claimed in claim 13 wherein said milled cartilage is hyaline and fibrosus cartilage.

17. A sterile cartilage repair material as claimed in claim 13 wherein said implant material includes an additive consisting of one or more of a group consisting of growth factors, human allogenic cells, human allogenic bone marrow cells, human autologous bone marrow cells, human allogenic stem cells, human autologous stem cells, demineralized bone matrix, and insulin.

18. A sterile cartilage repair material as claimed in claim 17 wherein said growth factors are one or more of a group consisting of FGF-2, FGF-5, IGF-1, TGF-β, BMP-2, BMP-7, PDGF, VEGF.

19. A sterile cartilage defect implant material as claimed in claim 13 wherein said milled cartilage ranges from about 25% to about 50% by weight and said carrier ranges from about 75% to about 50% by weight.

20. A sterile cartilage defect implant material as claimed in claim 13 wherein said milled cartilage ranges from about 15% to about 30% by weight with the carrier ranging from about 85% to about 70% by weight.

21. A sterile cartilage defect implant material comprising lyophilized milled allograft articular cartilage pieces ranging from 0.01 mm to 1.0 mm in size in a bioabsorbable carrier taken from a group consisting of sodium hyaluronate, hyaluronic acid and its derivatives, gelatin, collagen, chitosan, alginate, buffered PBS, Dextran or polymers and autologous bone marrow cells in an amount exceeding the natural occurrence of same in a patient being treated.

22. A sterile cartilage defect repair material as claimed in claim 21 including an additive in said implant material which consists of one or more of a group consisting of growth factors, human allogenic cells, autologous chondrocytes, demineralized bone matrix, and insulin.

23. A sterile cartilage repair material as claimed in claim 22 wherein said growth factors are one or more of a group consisting of FGF-2, FGF-5, IGF-1, TGF-β, BMP-2, BMP-7, PDGF, VEGF.

24. A sterile cartilage defect repair material as claimed in claim 21 wherein said bioabsorbable carrier consists of sodium hyaluronate, hyaluronic acid and its derivatives.

25. A sterile cartilage defect material as claimed in claim 21 wherein said lyophilized cartilage pieces have a water content ranging from about 0.1% to 8.0%.

26. A sterile cartilage defect implant material as claimed in claim 21 wherein said allograft articular cartilage is hyaline cartilage.

27. A sterile allograft cartilage defect implant material as claimed in claim 21 wherein said milled cartilage is fibrous cartilage.

28. A sterile allograft cartilage defect implant material as claimed in claim 21 wherein said milled cartilage is hyaline and fibrous cartilage.

29. A sterile cartilage defect implant material as claimed in claim 21 wherein said milled cartilage ranges from about 25% to about 50% by weight and said carrier ranges from about 75% to about 50% by weight.

30. A sterile cartilage defect implant material as claimed in claim 21 wherein said milled cartilage ranges from about 15% to about 30% by weight with the carrier ranging from about 85% to about 70% by weight.

31. A sterile cartilage defect implant material comprising lyophilized milled allograft articular cartilage pieces ranging from 0.01 mm to 1.0 mm in size in a bioabsorbable carrier taken from a group consisting of sodium hyaluronate, hyaluronic acid and its derivatives, gelatin, collagen, chitosan, alginate, buffered PBS, Dextran or polymers and autologous stem cells in an amount exceeding the natural occurrence of same in a patient being treated.

32. A method of placing a cartilage defect material in a cartilage defect, said cartilage defect material comprising milled allograft articular cartilage which has been lyophilized and mixed in a bioabsorbable carrier comprising the steps of:
  (a) cutting a patient's tissue at a site of a cartilage defect to remove a diseased area of cartilage;
  (b) adding autologous cells to said mixture of milled allograft cartilage in a bioabsorbable carrier;
  (c) placing a mixture of milled allograft cartilage with added autologous cells in a bioabsorbable carrier in the cartilage defect area where cartilage has been removed; and
  (d) placing a cover over the mixture of milled allograft cartilage in a bioabsorbable carrier to contain the mixture in cartilage defect site for a predetermined period of time.

33. The method of claim 32 wherein growth factors are added to said mixture.

34. The method of claim 32 wherein said autologous cells are chondrocytes.

35. The method of claim 32 wherein said autologous cells are bone marrow cells.

36. The method of claim 32 wherein said autologous cells are stem cells.

37. A sterile cartilage defect implant material comprising lyophilized milled allograft articular cartilage pieces ranging from 0.01 mm to 1.0 mm in size in a bioabsorbable carrier taken from a group consisting of sodium hyaluronate, hyaluronic acid and its derivatives and chitosan and autologous chondrocytes in an amount exceeding the natural occurrence of same in articular cartilage, wherein said milled cartilage ranges from about 25% to about 50% by weight and said bioabsorbable carrier ranges from about 75% to about 50% by weight.

38. A sterile cartilage defect implant material comprising lyophilized milled allograft articular cartilage pieces ranging from 0.01 mm to 1.0 mm in size in a bioabsorbable carrier taken from a group consisting of gelatin, collagen and alginate and autologous chondrocytes in an amount exceeding the natural occurrence of same in articular cartilage, wherein said milled cartilage ranges from about 25% to about 50% by weight and said bioabsorbable carrier ranges from about 75% to about 50% by weight.

39. A sterile cartilage defect implant material comprising lyophilized milled allograft articular cartilage pieces ranging from 0.01 mm to 1.0 mm in size in a bioabsorbable carrier taken from a group consisting of buffered PBS, Dextran or polymers and autologous chondrocytes in an amount exceeding the natural occurrence of same in articular cartilage, wherein said milled cartilage ranges from about 25% to about 50% by weight and said bioabsorbable carrier ranges from about 75% to about 50% by weight.

* * * * *

UNITED STATES PATENT AND TRADEMARK OFFICE
CERTIFICATE OF CORRECTION

| | | |
|---|---|---|
| PATENT NO. | : 7,067,123 B2 | Page 1 of 1 |
| APPLICATION NO. | : 10/424765 | |
| DATED | : June 27, 2006 | |
| INVENTOR(S) | : Katherine A. Gomes et al. | |

It is certified that error appears in the above-identified patent and that said Letters Patent is hereby corrected as shown below:

On the title page, Item (54), before "GLUE", insert --NOVEL--.

On the title page, Item (75), insert --William W. Tomford, Belmont, MA-- as an inventor.

Column 1, line 1, before "GLUE", insert --NOVEL--.

Column 7, line 67, after "restrictive," insert, --Variations and changes may be made by others without departing from the scope of the present invention as defined by the following claims:--.

Signed and Sealed this

Thirteenth Day of April, 2010

David J. Kappos
*Director of the United States Patent and Trademark Office*